United States Patent [19]
Ichida et al.

[11] Patent Number: 6,017,884
[45] Date of Patent: Jan. 25, 2000

[54] METHOD FOR TREATING ACUTE HEPATIC FAILURE

[75] Inventors: Fumihiro Ichida, Niigata; Miki Miyagiwa, Toyama, both of Japan

[73] Assignee: Sumitomo Pharmaceuticals Company, Limited, Osaka, Japan

[21] Appl. No.: 09/068,750

[22] PCT Filed: Oct. 4, 1996

[86] PCT No.: PCT/JP96/02890

§ 371 Date: May 15, 1998

§ 102(e) Date: May 15, 1998

[87] PCT Pub. No.: WO97/17991

PCT Pub. Date: May 22, 1997

[30] Foreign Application Priority Data

Nov. 15, 1995 [JP] Japan .................................. 7-322254

[51] Int. Cl.[7] .................................................. A61K 38/27
[52] U.S. Cl. .................................. 514/12; 514/2; 514/21; 514/810; 514/811; 514/893; 514/894; 435/69.1
[58] Field of Search .................................. 514/21, 12, 2, 514/810, 811, 893, 894; 435/69.1

[56] References Cited

U.S. PATENT DOCUMENTS

| 4,816,439 | 3/1989 | Jorgensen ................................ 514/12 |
| 5,096,885 | 3/1992 | Pearlman et al. ........................ 514/12 |
| 5,492,891 | 2/1996 | Skakkebaek et al. ................... 514/12 |

OTHER PUBLICATIONS

Miyagiwa et al., *Acta Hepatologica Japonica*, vol. 36, suppl. (3):78 (Oct. 1995) (with translation).

Asakawa et al., *J. Endocrinol. Invest.*, 12:343–347 (1989) (relevant description attached).

*Primary Examiner*—F. T. Moezie
*Attorney, Agent, or Firm*—Birch, Stewart, Kolasch & Birch, LLP

[57] ABSTRACT

The present invention provides a novel method for treating acute hepatic failure comprising administering a therapeutically effective amount of human growth hormone (hGH) to a patient suffering from the acute hepatic failure as well as a novel therapeutic agent for acute hepatic failure comprising the human growth hormone as an active ingredient.

6 Claims, 1 Drawing Sheet

METHOD FOR TREATING ACUTE HEPATIC FAILURE

This application is the national phase under 35 U.S.C. § 371 of prior PCT International Application Ser. No. PCT/JP96/02890, which has an International filing date of Oct. 4, 1996, which designated the United States of America, the entire contents of which are hereby incorporated by reference.

TECHNICAL FIELD

The present invention relates to a therapeutic agent for acute hepatic failure.

DESCRIPTION OF RELATED ART

Fulminant hepatitis (an acute or subacute type), which is a typical disease belonging to acute hepatic failure, is a severe hepatopathy caused by hepatitis viruses or medicaments. Fulminant hepatitis involves extensive necrosis and drop out of hepatic cells and its fatality rate is very high. Clinically, fulminant hepatitis is classified into acute type and subacute type, and life-saving rate in most-advanced medical spots is about 50% in the case of acute type and less than 10% in the case of subacute type. Autoimmune hepatitis and Wilson's disease (abdominal type) are known as analogous diseases of fulminant hepatitis [*Kon-nichi no Chiryoshishin* 1995, supervised by Shigeaki Hinohara et. al., Igaku-Shoin, Vol. 37, 378 (1995)].

Glucagon-insulin treatment and plasma exchange treatment have conventionally been performed for treating fulminant hepatitis, and their therapeutic effects are confirmed to some extent, although the effects are insufficient as mentioned above. Immunosuppressive therapy using immunosuppressive agents and hepatic cells protection therapy using prostaglandin have also been investigated. However, they have not yet been acknowledged as extraordinary effective therapeutic methods for fulminant hepatitis.

Hepatectomy, which is performed for treating hepatic carcinoma, causes acute hepatic failure, and therefore, extended hepatectomy exceeding 70% is regarded dangerous at present.

On the other hand, human growth hormone (hereinafter referred to as "hGH") is a proteinaceous hormone which has been used, since 1980's, for promoting growth of children suffering from pituitary dwarfism. Since hGH has an anabolism promoting activity, pharmaceutical uses thereof, for improvement of malnutrition state, promotion of wound healing, and the like are investigated, and it is reported that hGH has stimulated regeneration of hepatic cells in a hepatectomized rat [*Nihon Naibunpitsu Gakkai Zasshi*, Vol. 63, 9, 1123 (1989)]. However, hGH has been neither anticipated that it would be effective in therapy of acute hepatic failure such as fulminant hepatitis, nor investigated for that purpose [94/95 Nikkei Bio nenkan]. It is reported and well known that hGH has hepatic cells proliferation promoting activity in hypophysectomized rats. However, it merely suggests that administration of exogenous hGH can improve hepatatrophia caused by hGH deficiency and does not show usefulness of hGH administration for acute hepatic failure which generally shows increased hGH condition.

SUMMARY OF THE INVENTION

The subject of this invention is to provide a novel therapeutic agent for treating acute hepatic failure, and to provide a method for effective use thereof.

DETAILED DESCRIPTION OF THE INVENTION

In such a situation as described above, the present inventors investigated the administration of medicaments having hepatic cells regenerating activity in order to save patients suffering from acute hepatic failure to whom conventional therapeutic methods such as glucagon-insulin treatment are ineffective. Patients suffering from acute hepatic failure exhibited high hGH level in blood, which suggested that natural hepatic regenerating system already functioned at the maximum degree. However, when hGH was injected to patients to obtain extremely higher blood level of hGH than in physiological condition, liver function parameters of the patients were surprisingly improved, and remarkable improvements of systemic symptoms, such as decrease of abdominal dropsy, were also observed.

Thus, the inventors obtained the good results in the therapy of acute hepatic failure by administration of hGH to the patients. The present invention has been accomplished based on this finding.

Remarkable hepatic cell protection/proliferation and improvement of liver function can be expected, by application of the therapeutic agent of the present invention, for patients who cannot be recovered by conventional therapeutic methods such as prostaglandin administration and glucagon-insulin treatment, whereby patients' lives are saved. In addition, this therapeutic agent provides a means to avoid the risk of elicitation of acute hepatic failure due to extended hepatectomy, which allows sufficient excision of hepatic carcinoma.

Thus, the present invention relates to a therapeutic agent for treating acute hepatic failure comprising human growth hormone as an active ingredient. The present invention is explained in detail bellow.

HGH is used in therapy for pituitary dwarfism at present, and various gene recombinant formulations are commercially available (somatotropin having a brand name of "Genotropin" and the like). Any kind of hGH may be used in the present invention so long as it has hGH activity. In view of antigenicity, mature hGH is preferable. However, purified preparation from natural hypophysis (brand name of "Crescormon" and the like), Met-hGH which has a methionine residue at N-terminal (brand name of "Somatonorm" and the like), and recombinant hGH variants are within the scope of the present invention so long as they have hGH activity.

The term "hGH activity" refers to comprehensive growth-promotion activity which grows all human tissues except for brain, in particular, bone, which are principally in growth stage. That is, the term refers to all or part of the known hGH physiological activities such as (1) growth-promotion of bone and cartilage via somatomedin (IGF-I) induction; (2) promotion of amino acids uptake into cells and protein synthesis, and suppression of proteolysis; (3) promotion of neutral fat metabolism; (4) promotion of saccharometabolism; (5) promotion of storage of electrolytes such as Na and K.

A pharmaceutical formulation containing the therapeutic agent of the invention may be liquid form and freeze-dried form, and formulation for subcutaneous administration is particularly preferred. Stabilizers and carriers known to the art can be used for parenteral formulations, and the formulations are preferably used in the form of isotonic solution when used. As pharmaceutically acceptable carriers, proteins from plasma such as albumin, amino acids such as glycine, and sugars such as mannitol, can be used. See Japanese Patent Publication (Tokuhyo) Hei 3-503764 disclosing suitable examples therefor.

The term "Acute hepatic failure" to which the therapeutic agent of the invention is applied means liver function disorders caused by extensive necrosis and drop out of hepatic cells and the disorders due to extended hepatectomy. The therapeutic agent of the invention can also be used even in the case wherein the hypophysis function is normal and hGH blood level is raised over its normal value in response to hepatolysis. Disorders included in acute hepatic failure are listed bellow. Definitions for the disorders which prevail in Japan as of 1995 are also added. However, the acute hepatic failure according to the present invention is not limited in any respect by the definitions [see Kon-nichi no Chiryo-shishin 1995, supervised by Shigeaki Hinohara et. al., Igaku-Shoin, Vol. 37, 378 (1995) and The Nanzando's Medical Dictionary, the 17th edition].

(1) Fulminant hepatitis: hepatitis caused by hepatic viruses or medicaments, which meets the conditions that it is accompanied by psychoneurotic symptoms including hepatic coma of grade II or more (which is the grade determined at Inuyama Symposium and the grade II is characterized by disturbance of consciousness) within 8 weeks from the onset of hepatitis and that prothrombin time is less than 40%.

(2) Acute exacerbation of acute hepatitis or of chronic hepatitis: acute hepatitis refers to the pathology which is induced in patients who is firstly infected with hepatitis viruses, such as hepatitis viruses A, B, C, D and E (HAV, HBV, HCV, HDV and HEV). Acute hepatitis is diagnosed by detection of the specific antibody (particularly IgM antibody) against each virus. Abnormally high level of transaminase, GOT dominance, severe jaundice, extension of prothrombin time, or extremely low value in hapaplastin test is a sign of exacerbation to fulminant hepatitis.

Chronic hepatitis refers to pathology case in which the abnormalities in main hepatic markers such as GOT and GPT continue for more than six months, and typical chronic hepatitis includes chronic hepatitis B and C.

(3) Autoimmune hepatitis: a chronic, diffuse, and inflammatory hepatic disorder wherein continuous autoimmune reaction in liver causes progressive hepatolysis. According to the criterion determined by Autoimmune Hepatitis Subcommittee of Ministry of Health and Welfare, it is a chronic active hepatitis and exhibits autoimmune phenomena (more than 2.5 g/dl of gamma globulin in blood, LE cell phenomenon, antinuclear antibody or LE test positive, complication of autoimmune diseases and the like).

(4) Acute alcoholic hepatitis: a hepatitis which generally arises when a heavy drinker increases his drinking quantity rapidly and continuously, and it exhibits pyrexia, increase of leucocyte, abdominal dropsy, jaundice, and occasionally disturbance of consciousness. Severe acute hepatic failure gives lethality extending to 35–75%.

(5) Hepatic disorder caused by extended hepatectomy: a liver function failure which arises after hepatectomy performed for the purpose of treating primary hepatic carcinoma or metastatic hepatic carcinoma (particularly in the case wherein non-cancerous liver less than 40% is maintained after the hepatectomy).

(6) Wilson's disease (abdominal type): inborn abnormality of copper metabolism which is characterized by there major symptoms, cirrhosis, progressive extrapyramidal symptom and Kayser-Fleischer limbus. Hepatic type (abdominal type) arises in childhood with accompanying hepatopathy and hemolysis.

Subcutaneous, intravenous, and intramuscular administration can be used for hGH, and subcutaneous administration is generally used.

Dosage of hGH should be determined according to the condition, age, and sexuality of particular patient. In general, hGH is administered in an amount of 5–50 units(IU)/week for one day to three months in maximum, and preferably 10–30 units(IU)/week for one day to two months in maximum.

As described above, the therapeutic agent of the present invention shows remarkable hepatic cell protecting/proliferating effect and liver function recovering effect in patients suffering from acute hepatic failure. As a result, unfavorable prognosis of patients which had always been observed in the past can be improved remarkably.

EXAMPLE

Figure 1:
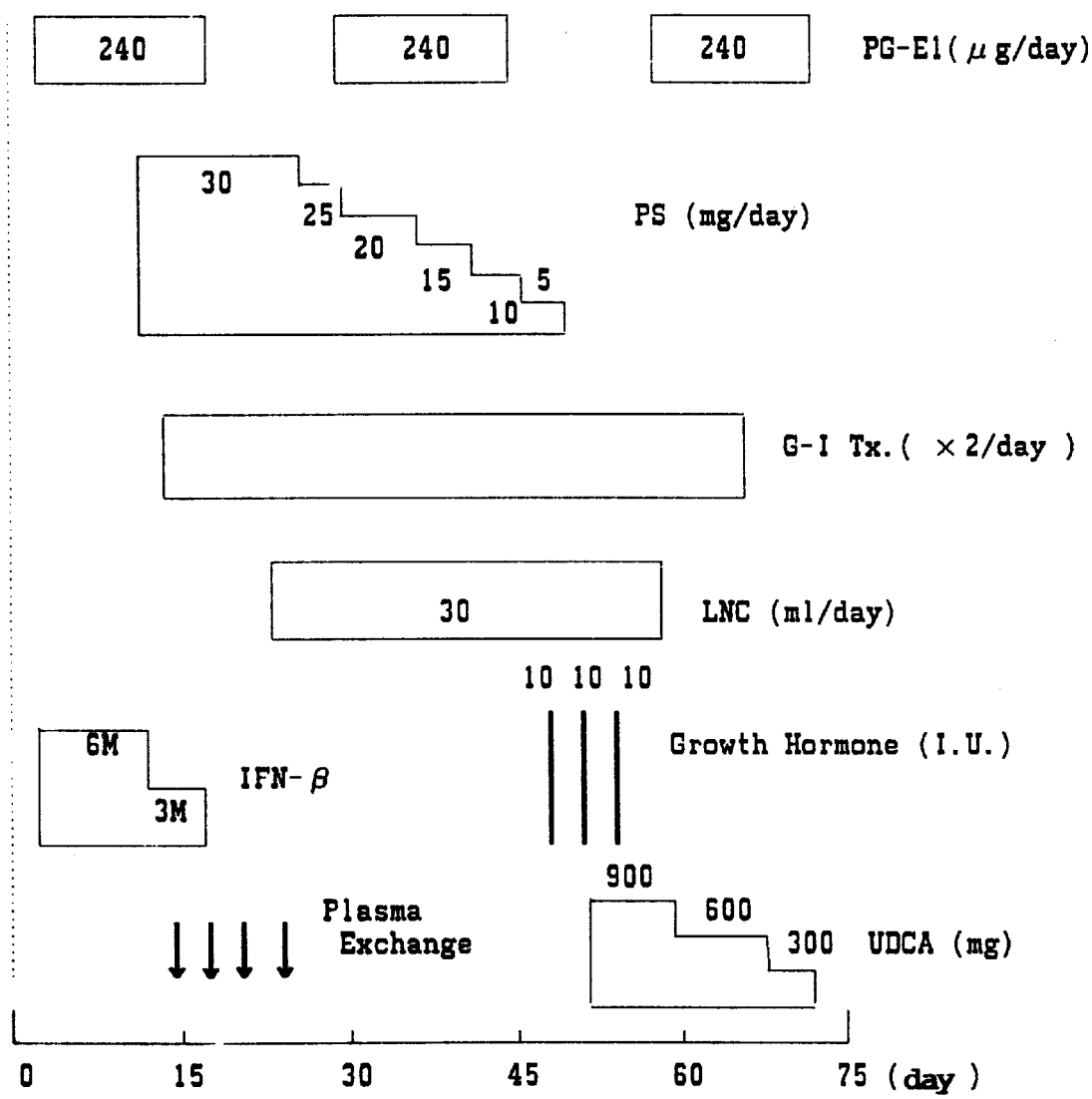
FIG. 1 shows the curative log after administration of hGH in Case 1. Abbreviations used in FIG. 1 have the following meanings.
[abbreviations]
PG-E1: alprostagil (Prostandin, Ono Pharmaceutical Co., Ltd.)
PS: prednisolone (Predonine, Shionogi & Co., Ltd.)
G-I Tx: glucagon insulin therapy
LNC: placenta hydrolysate (Laennec, Nippon Soaring)
UDCA: ursodeoxycholic acid (Urso, Tokyo Tanabe Co., Ltd.)
"Feron" (Daiichi Pharmaceutical Co., Ltd.) was used as interferon β and "Genotropin" (Sumitomo Pharmaceutical Co., Ltd.) was used as hGH.

The present invention is further explained by the following example.
Example:
Case 1. The patient was 44 years old, female. She had a cold symptom since Feb. 20, 1995. She had a medical check on February 27 because continuous abdominal distension feeling lasted. The physician pointed out that she exhibited GOT: 1407 U/L, GPT: 1064 U/L, T-Bil: 3.4 mg/ml, and therefore, she was hospitalized on March 1.
[Observations of the patient at the time of hospitalization]
150 cm tall, 49 kg body weight, body temperature 36.5° C., blood pressure 120/64, pulse 75/min as normal, lucid consciousness, no yellowed mucous membrane in eye bull, no palpebral conjunctival anaemia, dullness of liver at the right sixth intercostal space, palpability of liver at five finger breadths from midline and at three finger breadths from the right midclavicular line, somewhat stiff of liver elasticity. Spleen was not palpable. Abdominal dropsy and edema were not observed.
[Test Results of the patient at the time of hospitalization]
GOT: 1109 U/L; GPT: 1180 U/L; T-Bil: 5.5 mg/ml. Moderate increase in the biliary tract enzyme levels and slight hypoproteinemia were detected.
Prothrombin test (PT): 76%; hepaplastin test (HPT): 53%. Slight hypocoagulability.
Leukocyte count: 5,400/ mm$^2$; acidophil: 1%. No increase.
Virus marker: IgM type RA antibody (−); HA antibody (−); HBs antigen (−); HBs antibody (−); HBc antibody (+); HBe antigen (−); HBe antibody (+); DNA-P (−); HCV antibody (++). HCV-RNA measured on the eighth day after hospitalization (C-PCR method) (−). Autoantibody: (−).
[Therapy after hospitalization and process thereafter]
The patient was diagnosed as acute exacerbation of chronic hepatitis C, and received prostaglandin E1 for hepatic protection and interferon β for therapy of hepatitis C, and then the patient was subjected to glucagon-insulin (GI) treatment and mass administration of Laennec for the purpose of hepatic regeneration.

As a result, a serum transaminase level was lowered after it increased until its single peak on the 13th day. Lower HPT level around 20% continued and the serum T-Bil level temporally got better. However it increased again, which showed aggravation of the condition of the patient. In addition, steroid administration and plasma exchange treatment were also conducted as showed in FIG. 1. However, these treatments were not helpful for recovering the bad condition of the patient.

[HGH administration and process thereafter]

When HPT level lowered less than 20% on the 48th day, administration of hGH was started for the purpose of hepatic regeneration. HGH was administered three times in one week with each dose of 10 IU (total 30 IU) in the form of a pharmaceutical formulation for subcutaneous administration (10 IU of Genotropin; Pharmacia K.K.). As a result, decrease of abdominal dropsy pool, and subsequent reduction of serum T-Bil level followed by recovery of HPT level were observed as shown in Table 1.

TABLE 1

Change of biochemical parameters before and after hGH administration in Case 1.

|  | T-Bil | HPT |
| --- | --- | --- |
| before hGH administration (on April 19) | 15.1 mg/dl | 15% |
| after hGH administration 1 (on April 27) | 14.5 mg/dl | 17% |
| after hGH administration 2 (on May 6) | 8.5 mg/dl | 16% |
| after hGH administration 3 (on May 15) | 3.9 mg/dl | 37% |

[abbreviations]
T-Bil: serum total bilirubin level
HPT: Hepalastin test as an index of blood coagulability.

GI treatment, administration of hepatic protecting agents (alprostagil, ursodeoxycholic acid) were discontinued because improvement of the symptom as well as improvement of the biochemical parameters due to hGH administration were observed. Good symptom of the patient was kept stable and the patient left the hospital.

Pharmaceutical formulations:

A freeze-dried pharmaceutical formulation for subcutaneous administration, which is a typical formulation among hGH pharmaceutical formulations used in the present invention, may be produced in the following manner.

(1) In addition of 1 mg of purified recombinant hGH, 0.34 mg of glycine, 9 mg of mannitol, and 0.2 mg of Polysorbate 80 as a nonionic detergent are dissolved in 1 mL of phosphate buffer (pH 7.4, 5 mM).

(2) The resultant solution is freeze-dried. For the production of the above formulation, 50–200 times of glycine as a stabilizer, 700–3000 times of mannitol and 0.7–30 times of polysorbate 80 with respect to hGH in mole ratio are preferably used, and preferred pH of the buffer is from 4 to 8.

Effect of the Invention

The therapeutic agent of the present invention shows remarkable hepatic cell protecting/proliferating effect and liver function recovering effect in patients suffering from acute hepatic failure. As a result, unfavorable prognosis of patients which had always been observed in the past can be improved remarkably.

What we claim is:

1. A method for treating acute hepatic failure comprising administrating a therapeutically effective amount of human growth hormone to a patient suffering from the acute hepatic failure.

2. The method according to claim 1, wherein said administering is subcutaneously.

3. The method according to claim 1, wherein said administering is intravenously.

4. The method according to claim 1, wherein said administering is intramuscularly.

5. The method according to claim 1, wherein said effective amount is 5–50 (IU)/week for one day to three months.

6. The method according to claim 5, wherein said effective amount is 10–30 (IU)/week for one day to three months.

* * * * *